United States Patent [19]

Günter

[11] 4,124,589
[45] Nov. 7, 1978

[54] BENZIMIDAZO-[1,2-A]-QUINOLINES

[75] Inventor: Dieter Günter, Kelkheim, Taunus, Fed. Rep. of Germany

[73] Assignee: Hoechst Aktiengesellschaft, Frankfurt am Main, Fed. Rep. of Germany

[21] Appl. No.: 665,259

[22] Filed: Mar. 9, 1976

[30] Foreign Application Priority Data

Mar. 11, 1975 [DE] Fed. Rep. of Germany ....... 2510528

[51] Int. Cl.² .......................................... C07D 471/04
[52] U.S. Cl. ...................................... 546/70; 546/48; 546/52; 546/41
[58] Field of Search ........ 260/287 C, 289 C, 288 CF, 260/283 CF, 283 CN, 283 S, 286 R

[56] References Cited

U.S. PATENT DOCUMENTS 3,644,369  2/1972  Houlihan et al. ................. 260/287 C
3,894,029  7/1975  Winterfeldt et al. ............. 260/287 C

OTHER PUBLICATIONS

Morgan et al. I, "J. Chem. Soc.", (1938) p. 1292 ff.

ibid. II (1939) p. 1057ff.

Primary Examiner—Donald G. Daus
Assistant Examiner—David E. Wheeler
Attorney, Agent, or Firm—Curtis, Morris & Safford

[57] ABSTRACT

Benzimidazo-[1,2-a]-quinolines, of the general formula

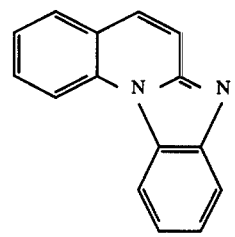

which may be substituted, are prepared by reacting 2-alkoxy-benzaldehydes with 2-phenylsulfonylmethylene-benzimidazoles. The compounds are strongly fluorescing and can be used as optical brighteners and fluorescent dyestuffs.

9 Claims, No Drawings

BENZIMIDAZO-[1,2-A]-QUINOLINES

The present invention relates to benzimidazo-[1,2-a]-quinolines and to a process for their preparation.

It is known that compounds of the series of the benzimidazo-[1,2-a]-quinolines are prepared from 2-aminoquinoline and picric acid (cf. G. Morgan, J. Stewart, J. Chem. Soc. 1295 (1938)). However, the process taught in this reference can be carried out only with picric acid as starting compound.

The present invention provides new benzimidazo-[1,2-a]-quinolines of the general formula I in which
$R_1$ is hydrogen, a lower alkyl or alkoxy radical, a halogen, nitro, amino, acylamino, lower mono- or dialkylamino-, lower trialkylammonium group or a carboxy or sulfo group optionally having modified functions,
$R_2$ is hydrogen or a carboxyl group, optionally having modified functions,
$R_3$ and $R_4$ each is hydrogen, hydroxy, amino, acetyl amino, a lower alkyl or alkoxy, nitro, amino, acylamino or a carboxyl group optionally having modified functions,
$R_5$ is hydrogen, a lower alkyl or carboxyl group optionally having modified functions,
$R_6$ is hydrogen, a lower alkyl or alkoxy group or a carboxyl group optionally having modified functions,
$R_7$ is hydrogen, a cyano, phenylsulfonyl or acetyl group, and two adjacent radicals $R_2$, $R_3$, $R_4$, $R_5$ together may form a fused phenyl ring and $R_6$ and $R_7$ together may form a fused 1,2,3-triazole ring, provided that $R_7$ is a phenysulfonyl group only when $R_6$ is a hydrogen atoms.

The term "lower" or "low molecular" in the above definitions with reference to aliphatic radicals is herein meant to be radicals having up to 6 carbon atoms, preferably up to 4, and especially up to 2 carbon atoms. Carboxyl groups having modified functions are the cyano group, the carboxylic acid ester group, especially phenyl ester and above all lower alkyl ester, in which case the lower alkyl esters may be substituted by hydroxy, lower alkoxy, lower dialkylamino or lower trialkylammonium groups; acid amides and acid hydrazides whose nitrogen atoms may be substituted by lower alkyl groups, two of those lower alkyl group being able to form together a saturated bivalent radical preferably, — together with the nitrogen atom which they are bound to — the pyrrolidine, piperidine, hexamethyleneimine, morpholine or piperazine radical.

Sulfo groups having modified functions are the sulfonic acid esters and the sulfonamides. Their definition is subject to the same conditions as mentioned for the carboxylic acid esters and the carbon amides cited above.

Preferred radicals $R_1$ to $R_7$ are the following:
$R_1$: H, $NO_2$, $NH_2$, $NHCH_3$, $NHC_2H_5$, $N(CH_3)_3$, $N(C_2H_5)_2$, $NHCOCH_3$, $CH_3$, $C_2H_5$, $OCH_3$, $OC_2H_5$,
$R_2$: H, COOH, $COOCH_3$, $COOC_2H_5$,
$R_3$: OH, $OCH_3$, $OC_2H_5$, $NHCONH_2$, $N(CH_3)_2$,
$R_4$: H, $OCH_3$,
$R_5$: H or $R_4$ and $R_5$ together with the carbon atoms which they are bound to are phenyl,
$R_6$: H and $R_7 = SO_2C_6H_5$ or
$R_6$: CN, COOH, $OCH_3$,
$R_7$: H, CN, COOH, $OCH_3$ or
$R_6$ and $R_7$: —N=N—NH—

The following compounds are preferred:

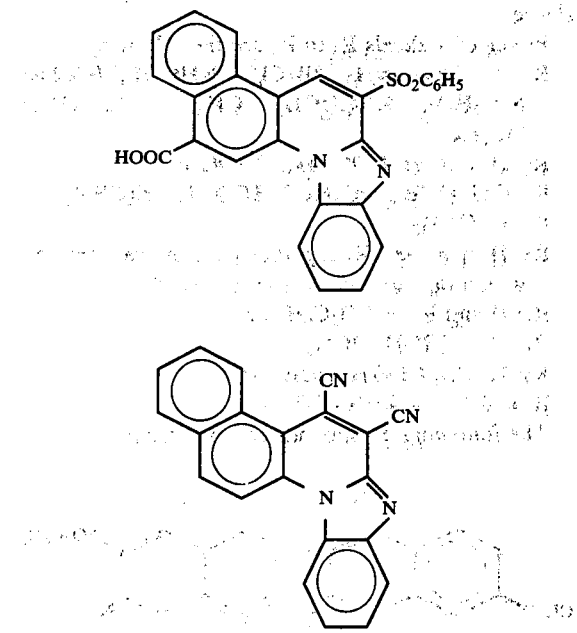

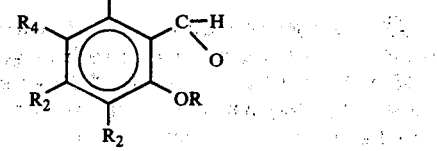

with 2-phenylsulfonylmethylene-benzimidazoles of the general formula III

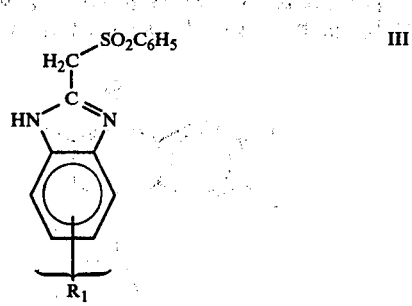

So, the compound of the formula IV is obtained.

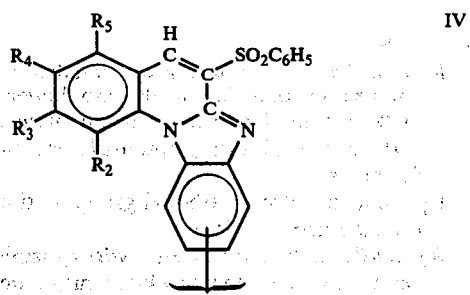

Other substituents $R_6$ and/or $R_7$ may then optionally be introduced by known addition-elimination reactions.

In formula II R is a hydrogen atom or a lower alkyl group, and the radicals $R_1$, $R_2$, $R_3$, $R_4$, $R_5$, $R_6$ and $R_7$ in the formulae II, III and IV are defined as in the formula I, the free amino group being excepted. They are prepared in known manner by starting either from the corresponding nitro compounds or the acetylamino compounds and reducing — preferably with iron in acid medium — or saponifying after condensation to obtain the desired compound of the formula I. Nitrile groups introduced as radicals $R_6$ and/or $R_7$ may also be saponified in known manner to yield the carboxyl group.

In the benzimidazoles of the formula III the positions 5 and 6 are equivalent. The nitrogen atoms in the imidazole ring are also equivalent. So, in the condensation of II + III → IV or I isomer mixtures as well as homogeneous substances may be obtained. Since the position of $R_1$ in the molecule of the formulae IV or I cannot be predetermined and has not been known so far, the position of $R_1$ has been characterized as shown above. The condensation of the compounds II and III is advantageously effected in a solvent forming azeotropic mixtures with the water formed in the course of the reaction, preferably an aromatic hydrocarbon, especially benzene, toluene, xylene or in chloro- or dichlorobenzene or in mixtures of those solvents, optionally with the addition of polar solvents, such as dimethylformamide or dimethyl sulfoxide as solution promoters. The The invention further provides a process for the preparation of the compounds of the formula I by reacting aldehydes of the general formula II reactants are generally used in stoichiometric amounts, an excess of the aldehyde of the formula II may optionally be used. The reaction is generally performed at normal pressure at temperatures ranging from 80° to 200° C. by adding catalytical amounts of, for example, piperazine acetate, sulfuric acid, p-toluenesulfonic acid or boric acid. Amounts of from 0.1–5% by weight, preferably 0.5–2% by weight, calculated on the aldehyde of the formula II are generally used.

The benzimidazo-[1,2-a]-quinolines of the formula I in which $R_6$ is H and $R_7$ is $SO_2C_6H_5$ generally precipitate from the solvents used as crystals and can so be separated easily in pure form. For the following introduction of other substituents $R_6$ and/or $R_7$ these benzimidazo-[1,2-a]-quinolines are reacted at temperatures ranging from 20° to 150° C. in solution or in suspension in aprotic solvents, for example dimethylsulfoxide, dimethylformamide, acetonitrile, sulfolane or phosphoric acid tris(dimethylamide) with alkali metal salts of nucleophilic anions, for example sodium cyanide, potassium cyanide, sodium methylate, sodium azide. In the compounds of the general formula IV in which $R_4$ and $R_5$ together are a fused phenyl ring, the substitution occurs in the $R_7$ position while the anion of the benzenesulfinic acid is split off. In all other cases, the anion occupies at first the $R_6$-position. When the reaction is carried out with twice the molar amount of these anions, those compounds may also be obtained in which the corresponding substituent is in the $R_6$ and the $R_7$ position. When proceeding in such a way, one of the anions mentioned may be introduced in the $R_6$-position in a first reaction step and in a second reaction step another anion may be introduced in the $R_7$-position, optionally while the anion introduced as $R_6$ is split off at the same time.

The isolation is effected in all cases by cooling, precipitation by crystallization and suction-filtering, optionally after concentrating the solvent.

The starting compounds of the formula III are prepared by reacting the corresponding substituted o-phenylene diamines with chloroacetic acid and following reaction in dimethylformamide with the sodium salt of the benzene sulfinic acids. Another method is described in the "Zeitschrift fur Chemie" 1968, page 385.

In the solid and dissolved state, the compounds of the invention are strongly fluorescing from reddish-blue to red depending on the substitution. The new compounds can be used as optical brighteners and as fluorescent dyestuffs. They are distinguished by a very good fastness to light.

Substrates which are to be brightened or dyed are for example lacquers, natural and synthetic fibers, such as those made of natural or regnerated cellulose, acetylcellulose, natural or synthetic polyamides, such as wool, polyamide-6 and -6,6; polyesters, polyolefins, polyvinyl chloride, polystyrene or polyacrylonitrile, foils, sheets and films, bands and shaped articles made from such materials.

The compounds of the invention which are insoluble in water may be used as solutions in organic solvents or in aqueous dispersions, advantageously with the aid of the usual dispersing agents.

Depending on the application field and the desired effect, the amount of the compounds of the general formula I to be used, calculated on the material to be brightened or dyed, may vary within wide limits. It can easily be evaluated by tests and is generally within the range of about 0.01 to 2% by weight.

The compounds of the formula I which contain one or several nitro groups, are generally not fluorescing alone, but they can be converted by reduction, for example with iron, into the fluorescent amino compounds in a one-step operation.

The following Examples illustrate the invention without limiting it thereto.

EXAMPLE 1

272 g (1 mol) of 2-phenylsulfonylmethylene-benzimidazole, 136 g (1 mol) of 2-methoxybenzaldehyde were heated in a 2 liter three-necked flask provided with thermometer, stirrer, cooler and water separator together with 10 g of pyridin acetate in a liter of toluene for three hours to the boil, 20.5 ml of water being separated in the water separator. Then the toluene was distilled off while adding at the same time 600 ml of o-dichlorobenzene. The mixture was stirred at 175° C. for 3 hours, cooled and suction-filtered. The residue was washed with acetonitrile. After drying at 60° C. under reduced pressure 322 g (90% of the theory) of green-yellow crystals were obtained which melted at 315°–316° C. A recrystallized sample of dimethyl formamide yielded a melting point of 317°–318° C. The reaction product had the formula

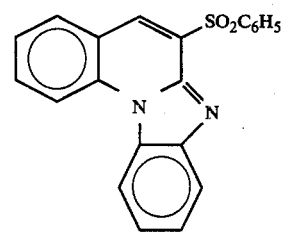

$C_{21}H_{14}O_2S$ molecular weight: 358.41
Absorption maximum: 346 nm
Fluorescence maximum: 475 nm in dimethylformamide.

EXAMPLE 2

107.6 g (0.3 mol) of the compound prepared according to Example 1 were suspended in 700 ml of dimethylsulfoxide and heated to 50° C. 15 g (0.306 mol) of sodium cyanide were added and the mixture was again stirred for 2 hours at 50° C. The mixture was cooled to −20° C., suction-filtered, and washed with acetonitrile. After drying, 60.7 g (83%) of slightly yellow crystals were obtained which melted at 255°–256° C. A recrystallized sample of dimethylformamide yielded the same melting point. The reaction had the formula

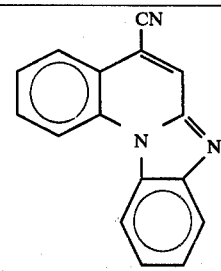

$C_{16}H_9N_3$ molecular weight: 243.25
Mass spectrum $M^+/e$: 243
Absorption maximum: 357 nm
Fluorescence maximum: 454 nm in dimethylformamide.

EXAMPLE 3

10 g (41 mols) of the compound prepared according to Example 2 were dissolved in 20 ml of concentrated sulfuric acid and 40 ml of water were added slowly. The mixture was stirred at 90° C. for 20 hours. 300 ml of ice water were added, the mixture was suction-filtered, washed with water until neutral and dried. 10 g (93% of the theory) of a nearly colorless compound were obtained which is soluble in alkali and had a melting point of 335° C. (decomposition). The compound had the formula

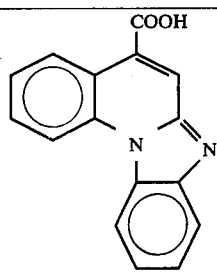

$C_{16}H_{10}O_2$ molecular weight: 262.27
Absorption maximum: 344 nm
Fluorescence maximum: 450 nm in dimethylformamide $C_{16}H_{10}O_2$ molecular weight: 262.27
Absorption maximum: 344 nm
Fluorescence maximum: 450 nm in dimethylformamide

EXAMPLE 4

3.6 g (10 mmols) of the compound prepared as in Example 1 were suspended in 50 ml of dimethylsulfoxide and heated to 50° C. After adding 1.3 g (20 mmols) of potassium cyanide the mixture was maintained at that temperature for 2 hours while stirring. After cooling to 20° C., the mixture was suction-filtered and washed with acetonitrile. 1.3 g of a yellow product were obtained which melted at 302°–305° C. After recrystallizing from methylglycol 1 g (37% of the theory) of a compound was obtained which melted at 308° C. and had the formula

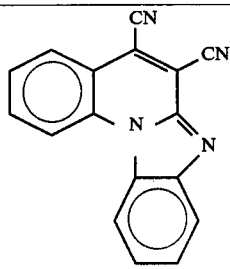

$C_{17}H_8N_4$   molecular weight 268.28
Mass spectrum $M^+/e = 268$
Absorption maximum:
Fluorescence maximum:   in dimethylformamide

EXAMPLE 5

81.7 g (0.3 mol) of 2-phenylsulfonylmethylenebenzimidazole and 49.9 g (0.3 mol) of 2,4-dimethoxybenzaldehyde were heated to the boiling temperature, while stirring, in 400 ml of toluene and 30 ml of dimethylformamide and 1 g of piperidine acetate was added. The mixture was stirred for 3 hours at the boiling temperature, 6 ml of water being separated. Then, toluene and dimethylformamide were distilled off and to the residue were added 400 ml of o-dichlorobenzene. After adding 0.5 g of boric acid, the mixture was again heated to 170° C. for 3 hours, then cooled, suction-filtered, washed with acetonitrile and dried. 110 g (94% of the theory) of a compound were added which melted at 318°–320° C. (A recrystallized sample of dimethylformamide melted at 318°–319° C.).

The reaction product had the formula

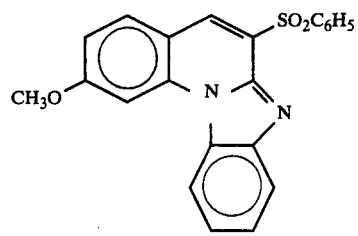

$C_{22}H_{16}N_2O_3S$   molecular weight: 388.44
Fluorescence maximum: 460 nm   in dimethylformamide.

EXAMPLE 6

35.1 g (90 mmols) of the compound prepared according to Example 5 were heated to 50° C. in 450 ml of dimethylsulfoxide. 4.9 g (0.1 mol) of sodium cyanide, dissolved in 30 ml of water were added, while stirring, in such a manner that 3 ml were added dropwise every 30 minutes. After adding the total amount of sodium cyanide, the mixture was again stirred for an hour at 50° C., then it was cooled, suction-filtered, washed with acetonitrile and dried. 23.4 g (95% of the theory) of a compound were obtained which melted at 240°–242° C. (A recrystallized sample of dimethylformamide melted at 243°–244° C.).

The reaction product had the formula

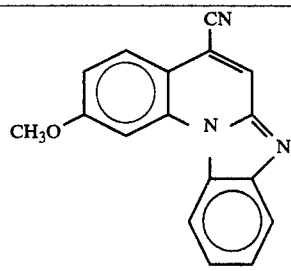

$C_{17}H_{11}N_6O$   molecular weight: 273.28
Mass spectrum: $M^+/e = .273$
Absorption maximum: 378 nm
Fluorescence maximum: 452 nm   in dimethylformamide

EXAMPLE 7

10.7 (30 mmols) of the compound prepared according to Example 1 were suspended in 80 ml of dimethylformamide and heated to 50° C. 1.8 g (30.6 mmols) of sodium methylate were added and the mixture was stirred at 50° C. for 4 hours, which yielded a homogeneous solution. The solvent was extracted over the rotation evaporator, the dark residue was washed with water and dried. It was purified with chloroform on a 50 cm silica gel column. 6.7 g of starting product were obtained. The 2.7 g of a compound which were obtained melted at 153°–154° C. after recrystallization from acetonitrile. It had the formula

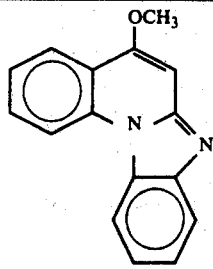

C$_{16}$H$_{12}$N$_2$O   molecular weight: 248.28
Mass spectrum: M$^+$/e = 248
Absorption maximum: 337 nm in dimethylformamide
Fluorescence maximum: 396 nm

EXAMPLE 8

68 g (0.25 mol) of 2-phenylsulfonylmethylene-benzimidazole were heated under reflux for 6 hours together with 46 g of 2-methoxy-1-naphthaldehyde, 2 g of piperidine-acetate and 400 ml of toluene, the water which had formed being centrifuged out. The mixture was cooled, suction-filtered, washed with acetonitrile and dried. 94.5 g (92% of the theory) of a compound were obtained which melted at >330° C. It had the formula

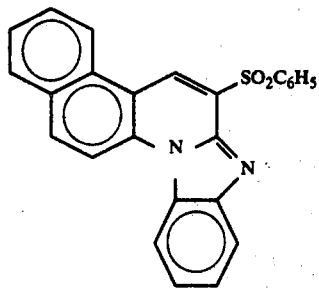

C$_{25}$H$_{16}$N$_2$O$_2$S    molecular weight: 408.47
Analysis:
Calculated:  C 73.5%; H 3.95%; N6.9%; O 7.8%; S 7.8%
Found        C 73.3%; H 4.0 %; N 7.2%; O 7.6%; S 7.5%.
Absorption maximum: 366 nm
Fluorescence maximum: 508 nm.

EXAMPLE 9

12.3 g (30 mmols) of the compound prepared according to Example 8 were suspended in 120 ml of dimethylsulfoxide and heated to 90° C. 1.5 g (30.6 mmols) of NaCN were added and the mixture was further stirred for 1 hour at 90° C. Filtering in the hot state followed. From the filtrate, 6.8 g of a compound crystallized out that melted at 281°–283° C. (after recrystallization from DMF the melting point was 283°–285° C.). The compound had the formula

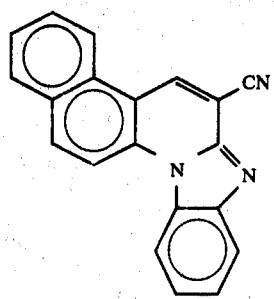

C$_{20}$H$_{11}$N$_3$ molecular weight: 293.33
Mass spectrum: M$^+$/e = 293
Absorption maximum: 363 nm
Fluorescence maximum: 500 nm in dimethylformamide

EXAMPLE 10

18 g (44 mmols) of the compound prepared according to Example 8 were heated to 120° C. while stirring, for 24 hours together with 3 g (45 mmols) of sodium azide in 500 ml of dimethylformamide. The mixture was filtered hot, the solvent was distilled off under reduced pressure, to the residue were added 200 ml of water and the whole was made neutral with 2 N HCl. After suction-filtering, washing with water and drying, 13 g (95% of the theory) of a compound were obtained which had the formula

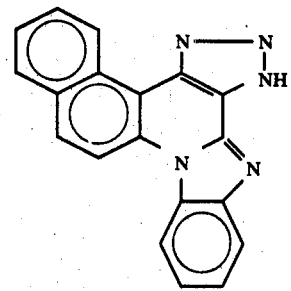

C$_{19}$H$_{11}$N$_5$ molecular weight: 309.32   melting point: >330° C
Analysis:
Calculated:   C 73.77%;   H 3.56;%   N 22.64%
Found:        C 73.3%;    H 3.6%;    N 22.4%
Absorption maximum: 290 nm    measured as potassium salt in
Fluorescence maximum: 423 nm   dimethylformamide

EXAMPLE 11

68 g (0.25 mol) of 2-phenylsulfonylmethylene-benzimidazole were heated under reflux for 8 hours with 43 g (0.25 mol) of 2-naphthol-1-aldehyde and 3 g of piperidine acetate in 400 ml of toluene and the water which had formed was centrifuged out. 9 ml of water were obtained. After cooling, the mixture was suction-filtered, washed with acetonitrile and dried. 90 g (88% of the theory) of a compound were obtained which was identical with that obtained according to Example 8.

EXAMPLE 12

32.6 g (78.5 mmols) of the compound prepared according to Example 9 were stirred for 1 hour at the boiling temperature in 1 liter of 8 N sulfuric acid and filtered through a filter heated with steam. After adding 1 l of water a thick precipitate was thrown down which was suction-filtered, suspended in 1 liter of water and adjusted to pH 9–10 with concentrated sodium hydroxide solution (36 ml) until constant pH. The mixture was suction-filtered, washed with water until neutral and dried at 60° C. under reduced pressure.
Yield: 26.4 g (90% of the theory) of the compound indicated in Example 23.

EXAMPLE 13

3.51 g (9 mmols) of the compound prepared according to Example 5 were heated to 90° C. in 45 ml of dimethylsulfoxide. 0.98 g (20 mmols) of sodium cyanide were added while stirring. The mixture was still stirred at 90° C. for 1 hour, it was cooled, suction-filtered and washed with acetonitrile. The residue was recrystallized from dioxane. 980 mg (40% of the theory) of a compound were obtained which melted at 255° C.

The reaction product had the formula

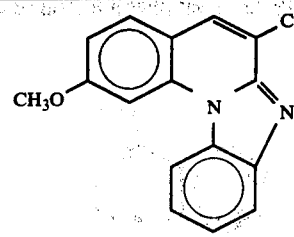

$C_{17}H_{11}N_6O$ molecular weight: 273.28
Mass spectrum: $M^+/e = 273$
Absorption maximum: 383 nm
Fluorescence maximum: 460 nm in dimethylformamide.

In analogy to the foregoing Examples, the following compounds were prepared:

| Example No. | Formula | Mass spectrum $M^+\gamma e$ | Absorpt. max. (nm) | Fluoresc. max. (nm) | Yield |
|---|---|---|---|---|---|
| 14 | [structure with $SO_2C_6H_5$ and $NHCOCH_3$ substituents] $C_{23}H_{17}O_3N_3S$ molecular weight 415.46 melting point 257° – 248° C | 415 | 362 | 495 | 70 |
| 15 | [structure with $SO_2C_6H_5$ and $CH_3$ substituents] $C_{22}H_{16}N_2O_2S$ molecular weight 372.44 melting point 332° – 334° C | | 353 | 481 | 60 |
| 16 | [structure with CN, HO, and $CH_3$ substituents] $C_{21}H_{14}N_2O_3S$ molecular weight 257.28 melting point 320° C | 374 | 379 | 462 | 55 |
| 17 | [structure with $CH_3O$, $CH_3O$, $SO_2C_6H_5$ substituents] $C_{23}H_{18}N_2O_4S$ molecular weight 418.46 | | 395 | 478 | 93 |

-continued

In analogy to the foregoing Examples, the following compounds were prepared:

| Example No. | Formula | Mass spectrum $M^+\gamma e$ | Absorpt. max. (nm) | Fluoresc. max. (nm) | Yield |
|---|---|---|---|---|---|
|  | melting point 340° C |  |  |  |  |
| 18 | 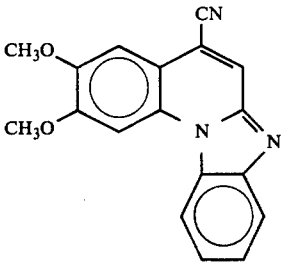<br>$C_{18}H_{13}N_3O_2$ molecular weight 303.3<br>melting point 315° – 317° C | 303 | 400 | 473 | 75 |
| 19 | 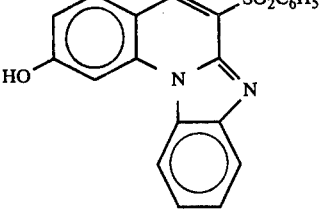<br>$C_{21}H_{14}N_2O_3S$ molecular weight 374.41<br>melting point >320° C | 374 | 379 | 462 | 55 |
| 20 | 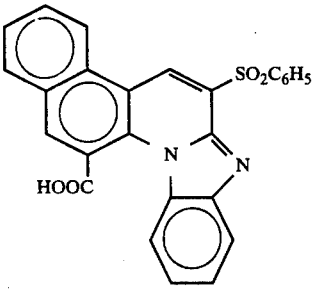<br>$C_{26}H_{16}N_2O_4S$ molecular weight 452.48<br>melting point >320° C |  | 378<br>415 | 515 | 75 |
| 21 | 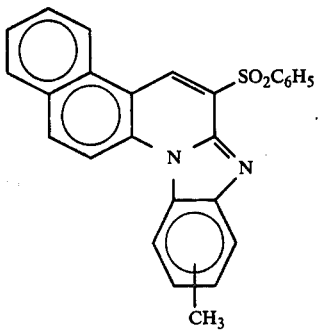<br>$C_{26}H_{18}N_2O_2S$ molecular weight 422.49<br>melting point >330° C |  | 361 | 506 | 87 |

-continued

In analogy to the foregoing Examples, the following compounds were prepared:

| Example No. | Formula | Mass spectrum M+γe | Absorpt. max. (nm) | Fluoresc. max. (nm) | Yield |
|---|---|---|---|---|---|
| 22 | C$_{21}$H$_{13}$N$_3$ molecular weight 307.33 melting point 283° – 285° C | | 370 | 510 | 74 |
| 23 | C$_{20}$H$_{12}$N$_2$O$_2$ molecular weight 312.32 melting point 288° C (decomposition) | | 361 406 | 485 | 92 |
| 24 | C$_{20}$H$_{14}$N$_2$O molecular weight 298.33 melting point 291° – 292° C | 298 | 363 382 | 424 | 25 |
| 25 | C$_{21}$H$_{13}$N$_3$O$_4$S molecular weight 403.41 melting point 317° – 318° C | | 338 | none | 83 |
| 26 | | 373 | | | 90 |

-continued

In analogy to the foregoing Examples, the following compounds were prepared:

| Example No. | Formula | Mass spectrum M+γe | Absorpt. max. (nm) | Fluoresc. max. (nm) | Yield |
|---|---|---|---|---|---|
|  | $C_{21}H_{15}N_3O_2S$ molecular weight 373.43 melting point >320° C |  |  |  |  |
| 27 | [structure with $SO_2C_6H_5$ and $NH_2$] $C_{25}H_{17}N_3O_2S$ molecular weight 423 melting point >320° C | 423 |  |  | 97 |
| 28 | [structure with CN and $NH_2$] $C_{16}H_{10}N_4$ molecular weight 258.29 melting point 278° – 80° C | 258 |  |  | 60 |
| 29 | [structure with $SO_2C_6H_5$ and $CH_3COHN$] melting point 321 – 322° C | 415 |  |  | 83% |
| 30 | [structure with $COCH_3$ and $CH_3COHN$] melting point 295° C | 317 | 392 |  | 64% |
| 31 | [structure with $SO_2C_6H_5$ and $H_2N$] melting point 322 – 324° C | 373 | 397; 416 |  | 86% |

-continued

In analogy to the foregoing Examples, the following compounds were prepared:

| Example No. | Formula | Mass spectrum M+/e | Absorpt. max. (nm) | Fluoresc. max. (nm) | Yield |
|---|---|---|---|---|---|
| 32 | 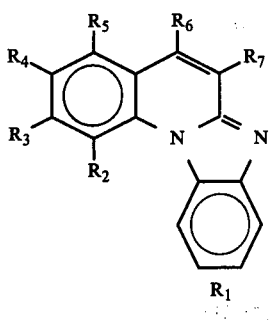 melting point 292 – 293° C | 298 | 430 | | 87% |

EXAMPLE 33

A fabric of polyethylene terephthalate was impregnated with a liquor which contained 1 g/l of the optical brightener of Example 2 in dispersed form. The textile material so treated was squeezed between rollers until it contained only 60% of its dry weight of liquid and then treated with hot air of 180° C. during 30 seconds. The fabric showed a degree of whiteness according to Berger of 121 (degree of whiteness = Y + 3 (Rz-Rx)). Moreover, the fabric was distinguished by an excellent fastness to light (6–7 according to DIN German Standards 54004).

EXAMPLE 34

A fabric of polyethylene terephthalate was introduced into a liquor in the ratio 1:40 which contained 1% of the fluorescent solid body of example 4. The cold liquor was heated to 125° C. during 30 minutes and maintained at that temperature during 30 minutes. After rinsing and drying, the fabric showed a fluorescent yellow-green shade (the liquor was practically extracted). The fastness to light was 7.

What is claimed is:

1. A benzimidazo-[1,2-a]-quinoline of the formula wherein
$R_1$ is a single substituent selected from the group of hydrogen, amino, lower alkanoylamino, nitro or lower alkyl;
$R_2$ is hydrogen or carboxyl;
$R_3$ is hydrogen, amino, acetamino, lower alkoxy or hydroxy;
$R_4$ is hydrogen or lower alkoxy;
$R_5$ is hydrogen or together with $R_4$ a fused benzene ring;
$R_6$ is cyano, hydrogen, carboxy or lower alkoxy and
$R_7$ is hydrogen, acetyl, cyano, carboxy, phenylsulfonyl or
$R_6$ and $R_7$ together are a fused 1,2,3-triazole ring, with the proviso that $R_7$ is phenylsulfonyl only when $R_6$ is hydrogen and at least one of $R_6$ and $R_7$ is other than hydrogen.

2. A compound as defined in claim 1, wherein
$R_1$ is hydrogen, amino, acetylamino, nitro or methyl;
$R_2$ is hydrogen or carboxyl;
$R_3$ is hydrogen, amino, acetamino, hydroxy or methoxy;
$R_4$ is hydrogen or methoxy;
$R_5$ is hydrogen or together with $R_4$ a fused benzene ring;
$R_6$ is hydrogen, cyano, carboxy or methoxy and
$R_7$ is hydrogen, acetyl, cyano, carboxy, phenylsulfonyl or
$R_7$ and $R_6$ together are a fused 1,2,3-triazole ring, with the proviso that $R_7$ is phenylsulfonyl only when $R_6$ is hydrogen.

3. A compound as defined in claim 1, wherein $R_1$, $R_2$, $R_4$ and $R_5$ are hydrogen.

4. The compound as claimed in claim 1, wherein $R_1$ and $R_2$ are hydrogen, $R_3$ is methoxy, $R_4$, $R_5$ and $R_6$ are hydrogen and $R_7$ is phenylsulfonyl.

5. The compound as claimed in claim 1, wherein $R_1$ and $R_2$ are hydrogen, $R_3$ is methoxy, $R_4$, $R_5$ and $R_6$ are hydrogen and $R_7$ is cyano.

6. The compound as claimed in claim 1, wherein $R_1$ and $R_2$ are hydrogen, $R_3$ is methoxy, $R_4$ and $R_5$ are hydrogen and $R_6$ and $R_7$ are cyano.

7. The compound as defined in claim 1, wherein $R_1$ and $R_2$ are hydrogen, $R_3$ is acetylamino, $R_4$, $R_5$ and $R_6$ are hydrogen and $R_7$ is phenylsulfonyl.

8. The compound as defined in claim 1, wherein $R_1$ and $R_2$ are hydrogen, $R_3$ is acetylamino, $R_4$, $R_5$ and $R_6$ are hydrogen and $R_7$ is acetyl.

9. The compound as claimed in claim 1, wherein $R_1$ and $R_2$ are hydrogen, $R_3$ is amino, $R_4$, $R_5$ and $R_6$ are hydrogen and $R_7$ is phenylsulfonyl.

* * * * *

UNITED STATES PATENT AND TRADEMARK OFFICE
CERTIFICATE OF CORRECTION

PATENT NO. : 4,124,589
DATED : November 7, 1978
INVENTOR(S) : Gunther

It is certified that error appears in the above—identified patent and that said Letters Patent are hereby corrected as shown below:

In the Heading, Item [75], "Günter" should be --Günther--;

Column 4, line 1, in the structural formula (II), the group "$\begin{smallmatrix}C-H\\ \backslash\\ O\end{smallmatrix}$" should be -- $\begin{smallmatrix}C-H\\ \backslash\backslash\\ O\end{smallmatrix}$ --.

Signed and Sealed this

Tenth Day of April 1979

[SEAL]

Attest:

RUTH C. MASON
Attesting Officer

DONALD W. BANNER
Commissioner of Patents and Trademarks